(12) United States Patent
Kumar et al.

(10) Patent No.: US 9,914,928 B2
(45) Date of Patent: Mar. 13, 2018

(54) G-RICH ISODNA SEQUENCES FORMING G-QUADRUPLEX STRUCTURE, THEIR FUNCTION AS APTAMERS AND A PROCESS FOR THE PREPARATION THEREOF

(71) Applicant: Council of Scientific & Industrial Research, New Delhi (IN)

(72) Inventors: Vaijayanti Anil Kumar, Pune (IN); Anita Dinkar Gunjal, Pune (IN); Moneesha Fernandes, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 15 days.

(21) Appl. No.: 14/893,928

(22) PCT Filed: May 23, 2014

(86) PCT No.: PCT/IN2014/000350
§ 371 (c)(1),
(2) Date: Nov. 24, 2015

(87) PCT Pub. No.: WO2014/188452
PCT Pub. Date: Nov. 27, 2014

(65) Prior Publication Data
US 2016/0194641 A1 Jul. 7, 2016

(30) Foreign Application Priority Data
May 24, 2013 (IN) .......................... 1561/DEL/2013

(51) Int. Cl.
*C12N 15/115* (2010.01)
*C07H 21/00* (2006.01)

(52) U.S. Cl.
CPC ...... *C12N 15/115* (2013.01); *C12N 2310/151* (2013.01); *C12N 2310/16* (2013.01); *C12N 2320/30* (2013.01)

(58) Field of Classification Search
CPC .............................. C12N 15/115; C07H 21/00
USPC ............... 435/6.1, 91.1, 455, 91.31; 514/44; 536/23.1, 24.2, 24.5
See application file for complete search history.

(56) References Cited

U.S. PATENT DOCUMENTS 5,840,867 A * 11/1998 Toole .................... C12Q 1/6811 435/6.1

FOREIGN PATENT DOCUMENTS

| WO | WO 03/002592 A1 | 1/2003 |
| WO | WO 2007/038869 A1 | 4/2007 |

OTHER PUBLICATIONS

Jung et al, J. Amer. Chem. Soc., vol. 116, No. 14, pp. 6059-6061 (1994).*
Prakash et al, Chem. Comm., vol. 15, pp. 1794-3-1794 (1996).*
Avino et al, Current Pharmaceutical Design, vol. 18, pp. 2036-2047 (2012).*
Abdel-Aziz et al., "Synthesis and Hybridization Property of Novel 2',5'-isoDNA Mimic Chiral Peptide Nucleic Acids," *Bioorg. Med. Chem. Lett.* (2003), 13(6):1041-1043, Elsevier Science Ltd.
Avino et al., "The Effect on Quadruplex Stability of North-Nucleoside Derivatives in the Loops of the Thrombin-Binding Aptamer," *Bioorg. Med. Chem.* (2012), 20(14):4186-4193, Elsevier Ltd.
Avino et al., "Thrombin Binding Aptamer, More than a Simple Aptamer: Chemically Modified Derivatives and Biomedical Applications," *Curr. Pharm. Design* (2012), 18(14):2036-2047, Bentham Science Publishers.
Baldrich and O'Sullivan, "Ability of Thrombin to Act as Molecular Chaperone, Inducing Formation of Quadruplex Structure of Thrombin-Binding Aptamer," *Anal. Biochem.* (2005), 341(1):194-197, Elsevier Inc.
Gunjal et al., "Functional isoDNA Aptamers: Modified Thrombin Binding Aptamers with a 2'-5'-Linked Sugar-Phosphate Backbone (isoTBA)," *Chem Commun.* (2014) 50(5):605-607.
Hannoush and Damha, "Remarkable Stability of Hairpins Containing 2',5'-Linked RNA Loops," *J. Am. Chem. Soc.* (2001), 123(49):12368-12374, American Chemical Society.
Jung and Switzer, "2',5'-DNA Containing Guanine and Cytosine Forms Stable Duplexes," *J. Am. Chem. Soc.* (1994), 116(14):6059-6061, American Chemical Society.
Nagatoishi et al., "Circular Dichroism Spectra Demonstrate Formation of the Thrombin-Binding DNA Aptamer G-Quadruplex under Stabilizing-Cation-Deficient Conditions," *Biochem. Biophys. Res. Commun.* (2007), 352(3):812-817, Elsevier Inc.
Prakash et al., "RNA Recognition by the 2'-Structural Isomer of DNA," *Chem. Commun.* (1996), 15:1793-1794.
Premraj et al., "Solution Structure of 2'5'd($G_4C_4$) Relevance to Topological Restrictions and Nature's Choice of Phosphodiester Links," *Eur. J. Biochem.* (2004), 271(14):2956-2966, FEBS.
Tang and Shafer, "Engineering the Quadruplex Fold: Nucleoside Conformation Determines Both Folding Topology and Molecularity in Guanine Quadruplexes," *J. Am. Chem. Soc.* (2006), 128(17):5966-5973.
Tucker et al., "G-Quadruplex DNA Aptamers and their Ligands: Structure, Function and Application," *Curr. Pharm. Design* (2012), 18(14):2014-2026, Bentham Science Publishers.
Wang et al., "A DNA Aptamer which Binds to and Inhibits Thrombin Exhibits a New Structural Motif for DNA," *Biochemistry* (1993), 32(8)1899-1904, American Chemical Society.

* cited by examiner

*Primary Examiner* — Jane J Zara
(74) *Attorney, Agent, or Firm* — DLA Piper LLP (US)

(57) ABSTRACT

The present invention relates to G-quadruplex forming isoDNA aptamers and a process for the preparation thereof. The present invention further relates to a stable, non-genetic, guanine rich 2'-5' linked isoDNA selected from 3' deoxy 2'-5' isoDNA and 3' deoxy 2'-5' isoDNA-isoRNA hybrid. The instant 2'-5' linked isoDNA such as the thrombin binding aptamer (isoTBA) can be used in deep vein thrombosis, where prolonged anticoagulant activity is required.

6 Claims, 11 Drawing Sheets

SEQUENCE LISTING

<160> NUMBER OF SEQ ID NOS: 10

<210> SEQ ID NO 1
<211> LENGTH: 15
<212> TYPE: DNA
<213> ORGANISM: Artificial Sequence
<220> FEATURE:
<223> OTHER INFORMATION: Unknown
<220> FEATURE:
<221> NAME/KEY: misc_feature
<223> OTHER INFORMATION: SELEX derived Thrombin binding aptamer

<400> SEQUENCE: 1
ggttggtgtg gttgg                                                         15

<210> SEQ ID NO 2
<211> LENGTH: 15
<212> TYPE: DNA
<213> ORGANISM: ARTIFICIAL SEQUENCE
<220> FEATURE:
<223> OTHER INFORMATION: 2.3' deoxy 2' -5' isoDNA oligomers
<220> FEATURE:
<221> NAME/KEY: misc_feature
<223> OTHER INFORMATION: 2. 3' deoxy 2' -5' isoDNA oligomers

<400> SEQUENCE: 2
ggttggtgtg gttgg                                                         15

<210> SEQ ID NO 3
<211> LENGTH: 15
<212> TYPE: DNA
<213> ORGANISM: ARTIFICIAL SEQUENCE
<220> FEATURE:
<223> OTHER INFORMATION: Unknown
<220> FEATURE:
<221> NAME/KEY: misc_feature
<223> OTHER INFORMATION: UGU loop-modified sequence isod-TBA-3
<220> FEATURE:
<221> NAME/KEY: misc_feature
<222> LOCATION: (7)..(9)
<223> OTHER INFORMATION: U at position 7 and position 9
<220> FEATURE:
<221> NAME/KEY: misc_feature
<222> LOCATION: (7)..(9)
<223> OTHER INFORMATION: "n" represents U at position 7 and position 9

<400> SEQUENCE: 3
ggttggngng gttgg                                                         15

<210> SEQ ID NO 4
<211> LENGTH: 14
<212> TYPE: DNA
<213> ORGANISM: ARTIFICIAL SEQUENCE
<220> FEATURE:
<223> OTHER INFORMATION: Unknown
<220> FEATURE:
<221> NAME/KEY: misc_feature
<223> OTHER INFORMATION: 2. 3' deoxy 2' -5' isoDNA oligomers

<400> SEQUENCE: 4
ggttggttgg ttgg                                                          14

<210> SEQ ID NO 5
<211> LENGTH: 13
<212> TYPE: DNA
<213> ORGANISM: ARTIFICIAL SEQUENCE
<220> FEATURE:
<223> OTHER INFORMATION: Unknown
<220> FEATURE:
<221> NAME/KEY: misc_feature -continued
<223> OTHER INFORMATION: 2. 3' deoxy 2'-5' isoDNA oligomers

<400> SEQUENCE: 5
ggtggtgtgg tgg                                                    13

<210> SEQ ID NO 6
<211> LENGTH: 11
<212> TYPE: DNA
<213> ORGANISM: ARTIFICIAL SEQUENCE
<220> FEATURE:
<223> OTHER INFORMATION: Unknown
<220> FEATURE:
<221> NAME/KEY: misc_feature
<223> OTHER INFORMATION: 3. 3' deoxy 2'-5' isoDNA-isoRNA hybrid aptamer

<400> SEQUENCE: 6
ggtggtggtg g                                                      11

<210> SEQ ID NO 7
<211> LENGTH: 15
<212> TYPE: DNA
<213> ORGANISM: ARTIFICIAL SEQUENCE
<220> FEATURE:
<223> OTHER INFORMATION: Unknown
<220> FEATURE:
<221> NAME/KEY: misc_feature
<223> OTHER INFORMATION: 3.3' deoxy 2'-5' isoDNA-isoRNA hybrid aptamer
<220> FEATURE:
<221> NAME/KEY: misc_feature
<222> LOCATION: (7)..(7)
<223> OTHER INFORMATION: XUF is 3'deoxy, 3'-xylofluoro-uridine
<220> FEATURE:
<221> NAME/KEY: misc_feature
<222> LOCATION: (7)..(7)
<223> OTHER INFORMATION: "n" represents XUF which is 3'deoxy,
      3'-xylofluoro-uridine

<400> SEQUENCE: 7
ggttggngtg gttgg                                                  15

<210> SEQ ID NO 8
<211> LENGTH: 15
<212> TYPE: DNA
<213> ORGANISM: ARTIFICIAL SEQUENCE
<220> FEATURE:
<223> OTHER INFORMATION: Unknown
<220> FEATURE:
<221> NAME/KEY: misc_feature
<223> OTHER INFORMATION: 3.3' deoxy 2'-5' isoDNA-isoRNA hybrid aptamer
<220> FEATURE:
<221> NAME/KEY: misc_feature
<222> LOCATION: (7)..(9)
<223> OTHER INFORMATION: "n" at position 7 and position 9 represents XUF
      which is 3'deoxy, 3'-xylofluoro-uridine

<400> SEQUENCE: 8
ggttggngng gttgg                                                  15

<210> SEQ ID NO 9
<211> LENGTH: 15
<212> TYPE: DNA
<213> ORGANISM: ARTIFICIAL SEQUENCE
<220> FEATURE:
<223> OTHER INFORMATION: Unknown
<220> FEATURE:
<221> NAME/KEY: misc_feature
<223> OTHER INFORMATION: 3.3' deoxy 2'-5' isoDNA-isoRNA hybrid aptamer
<220> FEATURE:
<221> NAME/KEY: misc_feature
<222> LOCATION: (7)..(7)
<223> OTHER INFORMATION: "n" is at position 7 represents rUF is 3'deoxy, 3'-ribofluoro-uridine.

<400> SEQUENCE: 9
ggttggngtg gttgg                                                    15

<210> SEQ ID NO 10
<211> LENGTH: 15
<212> TYPE: DNA
<213> ORGANISM: ARTIFICIAL SEQUENCE
<220> FEATURE:
<223> OTHER INFORMATION: Unknown
<220> FEATURE:
<221> NAME/KEY: misc_feature
<223> OTHER INFORMATION: 3.3' deoxy 2' -5' isoDNA-isoRNA hybrid aptamer
<220> FEATURE:
<221> NAME/KEY: misc_feature
<222> LOCATION: (7)..(9)
<223> OTHER INFORMATION: "n" at position 7 and 9 represents rUF which
      is 3'deoxy, 3'-ribofluoro-uridine.

<400> SEQUENCE: 10
ggttggngng gttgg                                                    15

G-RICH ISODNA SEQUENCES FORMING G-QUADRUPLEX STRUCTURE, THEIR FUNCTION AS APTAMERS AND A PROCESS FOR THE PREPARATION THEREOF

CROSS-REFERENCE TO RELATED APPLICATIONS

This application is a 35 USC § 371 National Stage application of International Application No. PCT/IN2014/000350 filed May 23, 2014, now pending; which claims the benefit under 35 USC § 119(a) to India Application No. 1561/DEL/2013 filed May 24, 2013. The disclosure of each of the prior applications is considered part of and is incorporated by reference in the disclosure of this application.

INCORPORATION OF SEQUENCE LISTING

The material in the accompanying sequence listing is hereby incorporated by reference into this application. The accompanying sequence listing text file, name LALL1430_Sequence_Listing.txt, was created on Mar. 9, 2016, and is 4 kb. The file can be assessed using Microsoft Word on a computer that uses Windows OS.

FIELD OF THE INVENTION

The present invention relates to the stable, non-genetic guanine rich 2'-5' linked iso DNA oligomers capable of forming unimolecular antiparallel G quadruplexes and a process of preparation thereof.

The present invention further relates to hybrids comprising 2'-5'-phosphodiester linkages as part of the G-quadruplex-forming sequence/oligomer.

BACKGROUND OF THE INVENTION

In molecular biology, G-quadruplexes (also known as G-tetrads or G4-DNA) are nucleic acid sequences that are rich in guanine and capable of forming a four-stranded structure (Shampay, J., Szostak, J. W., Blackburn, E. H. DNA sequences of telomeres maintained in yeast. Nature 310, 154-157). Four guanine bases associate through Hoogsteen hydrogen bonding to form a square planar structure called a guanine tetrad, and two or more guanine tetrads can stack on top of each other to form a G-quadruplex. They can be formed of DNA (Blackburn, E. H. Structure and function of telomeres. Nature 350, 569-573, 1991, Simonsson T. G-Quadruplex DNA Structures—Variations on a Theme Biol. Chem. 382, 621-628, 2001, Wang, K. Y., McCurdy, S., Shea, R. G., Swaminathan, S., Bolton, P. H. A DNA aptamer which binds to and inhibits thrombin exhibits a new structural motif for DNA. Biochemistry 32, 1899-904 1993) or RNA (Joachimi, A., Benz, A., Hartig, J. S. "A comparison of DNA and RNA quadruplex structures and stabilities". Bioorg. Med. Chem. 17, 6811-6815 (2009)) and may be intramolecular, bimolecular, or tetramolecular. Depending on the direction of the strands or parts of a strand that form the tetrads, structures are described as parallel or antiparallel. The G-quadruplex structures as telomeres at the chromosomal ends are meant for conservation of genetic information during repeating cell cycles and are also capable of specific interactions with proteins. DNA is a molecule that encodes the genetic instructions used in the development and functioning of all known living organisms and many viruses. In nature, DNA is based on 2'-deoxyribose and has its phosphate links between carbons 3' and 5' of adjacent nucleosides. It is however observed that 3'-deoxyribose is not a good basis for nucleosides to carry genetic information as a isoDNA. A stable duplex in DNA with mixed sequences is required, and 3'-deoxyribose in 2'-5' linked isoDNA does not form stable duplexes. isoDNA is studied in the art to achieve better stability of duplexes. The 3'-deoxy-2'-5'-linked isoDNA sequences are known to form duplexes with complementary RNA. However their thermal stability is lower compared to the DNA:DNA/DNA:RNA or RNA:RNA duplexes known in the art. One important structure often observed within single stranded G-rich DNA aptamers is the G-quadruplex. No such example exists in literature till today that the G-rich isoDNA can form a G-quadruplex structure. Szostak et. al in 'Functional RNAs exhibit tolerance for non-heritable 2'-5' versus 3'-5' backbone heterogeneity'; Nature—Chemistry 5, 390-394 (2013) discloses synthetic mixed-backbone RNA aptamers with randomly interspersed 2'-5' and 3'-5' phosphodiester linkages compatible for folding into defined three-dimensional structures such as stem-loop structure that retain molecular recognition with 10%-25% tolerance to 2'-5' doping heterogeneity in a 3'-5' backbone. However, Szostak et al provide a mixture of randomly interspersed 2'-5' and 3'-5' phosphodiester linkages in the backbone of RNA aptamers and do not provide RNA or DNA aptamers with solely 2'-5' phosphodiester linkages. Thrombin binding aptamer (TBA) is a SELEX derived aptamer sequence 5'-G1G2T3T4G5G6T7G8T9G10G11T12T13G14G15-3'. Backbone modifications of TBA are reported to have profound effects on the structural topology of the tetraplex formed. The folding patterns of an isosequential TBA RNA sequence showed that in contrast to the unimolecular antiparallel G-quadruplex structure of TBA (FIG. 2) (Wang, K. Y., McCurdy, S., Shea, R. G., Swaminathan, S., Bolton, P. H. A DNA aptamer which binds to and inhibits thrombin exhibits a new structural motif for DNA. Biochemistry 32, 1899-904, 1993). the RNA-TBA oligomer formed a multimolecular parallel G-quadruplex (FIG. 2). A mixed DNA/RNA backbone TBA sequence, depending on the position of the ribo- or deoxyribo-nucleotides in the sequence, either folded in DNA-like or RNA-like quadruplex structures. RNA-based SELEX against thrombin gave a completely different nucleobase sequence compared to DNA-TBA. The recently discovered 3'-2'-TNA (FIG. 1) aptamer against thrombin was G-rich sequence but not the same as TBA. The loop configuration of the quadruplex also can be the deciding factor of various structural topologies with varying loop configurations. It is evident from this discussion that the backbone element is the crucial governing entity for maintaining the functional structural quadruplex topology of any given sequence. Avino A et al in Bioorg Med Chem. 2012 Jul. 15; 20(14):4186-93, report the synthesis of modified thrombin-binding aptamers (TBAs) carrying uridine (U), 2'-deoxy-2'-fluorouridine (FU) and North-methanocarbathymidine (NT) residues in the loop regions. Replacement of thymidine in TGT loop by U and FU results in an increased stability of the antiparallel quadruplex structure of TBA. However, synthesis of 2'-5' linked isoDNA TBA comprising substitution of T by U in the TGT loop for anti-thrombin activity is not provided by Avino et al. In light of the above, there remains a need in the art to provide isoDNA oligomers that are capable of forming G-quadruplex structures which will be able to maintain biological molecular recognition and functional ability. Further, the evaluation of structural topology and stability of G-quadruplexes formed by isoDNA as functional molecule for use in therapeutics and diagnostics applications is of importance and relevance, which remain the objects of the invention.

OBJECT OF THE INVENTION

The main objective of the invention is to provide stable, non-genetic guanine rich 2'-5' linked iso DNA sequences capable of forming unimolecular antiparallel G quadruplexes.

Another objective of the invention is to provide the process of preparation of guanine rich 2'-5' linked iso DNA sequences Yet another objective of the invention is to provide the process of preparation of G-quadruplex forming isoDNA aptamers comprising a stable, non-genetic, guanine rich 2'-5' linked isoDNA sequence Another objective of the invention is to provide a composition comprising the guanine rich 2'-5' linked iso DNA sequences with one or more pharmaceutically acceptable excipients.

Yet another objective is to provide a method of treatment of deep vein thrombosis using thrombin binding aptamer (isoTBA) aptamer comprising a stable, non-genetic, guanine rich 2'-5' linked isoDNA,

SUMMARY OF THE INVENTION

Accordingly the present invention provides a G-quadruplex forming isoDNA aptamers comprising a stable, non-genetic, guanine rich 2'-5' linked isoDNA sequence selected from 3' deoxy 2'-5' isoDNA and 3' deoxy 2'-5' isoDNA-isoRNA hybrid.

In an embodiment of the present invention, the 2'-5' linked isoDNA sequence forms unimolecular antiparallel G quadruplexes.

In still another embodiment of the present invention, the 2'-5' linked isoDNA sequence optionally forms hybrids with isoRNA.

In yet another embodiment of the present invention, the 3' deoxy 2'-5' isoDNA sequence are selected from the group consisting of Seq ID No. 2
5'-GGTTGGTGTGGTTGG-2'

Seq ID No. 3
5'-GGTTGGUGUGGTTGG-2',

Seq ID No. 4
5'-GGTTGGTTGGTTGG-2',

Seq ID No. 5
5'-GGTGGTGTGGTGG-2'

Seq ID No. 6
5'-GGTGGTGGTGG-2'.

and the 3' deoxy 2'-5' isoDNA-isoRNA hybrid aptamer are selected from the group consisting of Seq ID No. 7
5'-GGTTGG$^X$U$^F$GTGGTTGG-2';

Seq ID No. 8
5'-GGTTGG$^X$U$^F$G$^X$U$^F$GGTTGG-2'

Seq ID No. 9
5'-GGTTGG'U$^F$GTGGTTGG-2'

Seq ID No. 10
5'-GGTTGG'U$^F$G'U$^F$GGTTGG-2'

In still another embodiment of the present invention, the 2'-5' linked isoDNA is a thrombin-binding aptamer (TBA) having Seq ID No. 2 or Seq ID No. 3.

In yet another embodiment of the present invention, the G-quadruplex forming isoDNA aptamer is useful for the preparation of a medicament for the treatment of deep vein thrombosis.

Another aspect of the present invention is a process for synthesis of G-quadruplex forming isoDNA sequence, wherein said process comprises the steps of:
 a) synthesizing 3'-5'-oligonucleotides having Seq ID No. 1 by β-cyanoethyl phosphoramidite chemistry;
 b) replacing the 3'-5'-phosphodiester linkages in Seq ID no. 1 (dTBA-1) by 2'-5'-phosphodiester linkages to obtain 3'-deoxy-2'-5' oligomer 5'-GGTTGGTGTGGT-TGG-2' Seq ID No 2 (isod-TBA-2);
 c) replacing 3'-deoxythymidine in the TGT loop (T7 and T9 in isod-TBA-2) by uridine to obtain UGU loop-modified sequence isod-TBA-3 (Seq ID No: 3); removing 3'deoxyguanosine (G) at position G8 (TGT loop) in sequence ID No 2, to obtain TT loop in 14 mer sequence having Seq ID No. 4; removing T4 and T13 in sequence ID No. 2 to obtain 13 mer sequence having Seq ID No. 5; removing T4, G8, T9 and T13 in sequence ID No 2 to obtain 11 mer sequence having Seq ID No. 6.
 d) desalting the oligonucleotides as obtained in step a to c after post-synthetic treatment by passing through G25 Sephadex columns followed by purification by RP-HPLC using an increasing gradient of acetonitrile in 0.1M triethylammonium acetate (pH 7.0);
 e) dissolving HPLC purified oligonucleotides as obtained in step d in phosphate buffer pH7.5 containing KCl followed by lyophilization and further dilution,
 f) replacing 3'-deoxythymidine in the TGT loop (T7 and T9) in isod-TBA-2 by uridine in a 2'-5'-linkage (using 3'-O-TBDMS-2'-phosphoramidite during synthesis) to obtain 'UG'U loop-modified sequence having Seq ID No: 7),
 g) replacing 3'-deoxythymidine in the TGT loop (T7 and T9) in isod-TBA-2 by 3% deoxy-3'-xylofluorouridine to obtain $^X$U$^F$G$^X$U$^F$ loop-modified sequence having Seq ID no: 8;
 h) replacing 3'-deoxythymidine in the TGT loop (T7) in isod-TBA-2 by 3'-deoxy-3'-ribofluorouridine to obtain 'U$^F$ loop-modified sequence having Seq ID no: 9;
 i) replacing 3'-deoxythymidine in the TGT loop (T7 and T9) in isod-TBA-2 by 3'-deoxy-3'-ribofluorouridine to obtain 'U$^F$ G'U$^F$ loop-modified sequence (Seq ID no: 10),
 j) forming G quadraplex by 2'-5' iso DNA sequences in presence of monovalent cations.
    In still another embodiment of the present invention is disclosed G-quadruplex formation by 2'-5'isoTBA sequences having sequence ID No 2 and 3 in the presence of thrombin.

In yet another embodiment of the present invention, wherein the phosphoramidites are selected from the group consisting of Uridine 3'-O-t. butyldimethylsilyl-2'-phosphoramidite and 3'deoxy-2'-phosphoramidites.

In still another embodiment of the present invention, a composition comprising the aptamer according to claim 1 with one or more pharmaceutically acceptable excipients.

In yet another embodiment of the present invention, a method of treatment of deep vein thrombosis comprising administering an effective amount of thrombin binding aptamer (TBA) aptamer comprising a stable, non-genetic, guanine rich 2'-5' linked iso DNA, optionally with one or more pharmaceutically acceptable excipients.

According to the invention, stable, non-genetic 2'-5' linked isoDNA oligomers capable of forming unimolecular antiparallel G quadruplexes maintain biological molecular recognition and is useful in therapeutics and diagnostics. The 2'-5' linked isoDNA is a thrombin-binding aptamer (TBA).

In another aspect, the present invention provides hybrids involving 2'-5'-phosphodiester linkages as part of the G-quadruplex-forming sequence/oligomer that could be in combination with 3'-5'-phosphodiester linkages in DNA, or other linkages such as in TNA, LNA, UNA, 3'-5'-linked modified backbones such as 2'-OMe, etc.

BRIEF DESCRIPTION OF DRAWING

FIG. 6b depicts induction time which is indicated as a coagulation parameter ($t_i$).

DETAILED DESCRIPTION OF THE INVENTION

Figure 1:
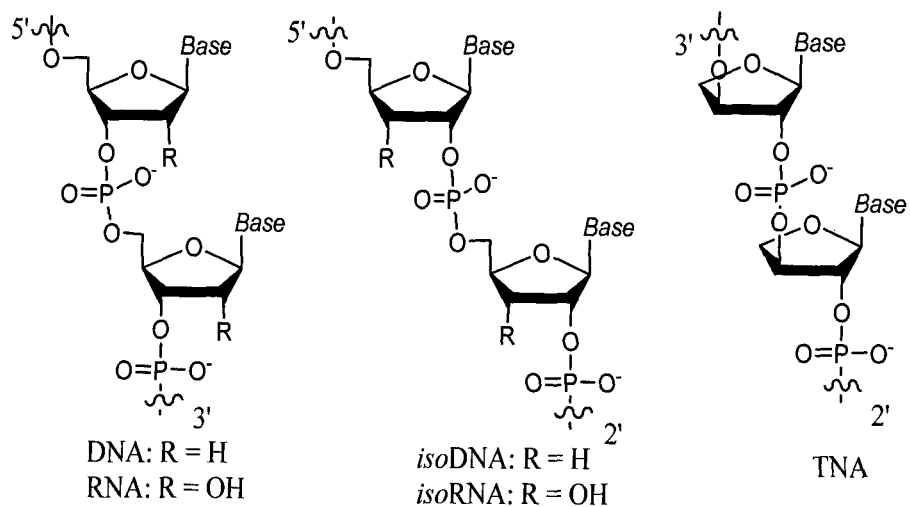
FIG. 1 depicts genetic 3'-5' DNA/RNA, non-genetic 2'-5'-iso DNA/RNA and 3'-2'TNA.
Figure 2:
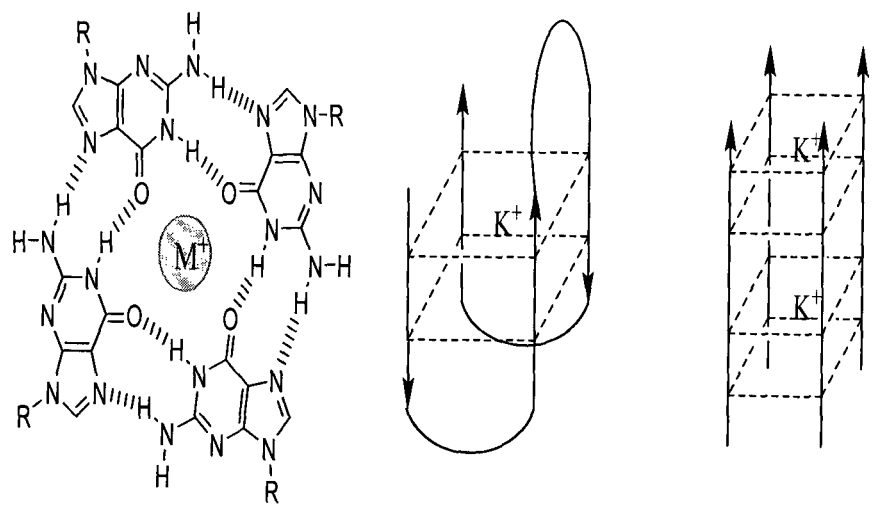
FIG. 2 depicts the schematic representation of the Guanine tetrad, antiparallel unimolecular G-quadruplex and multimolecular parallel G-quadruplex.

The invention will now be described in detail in connection with preferred and optional embodiments, so that various aspects thereof may be more fully understood and appreciated. As envisaged above, the backbone element is the crucial governing entity for maintaining the functional structural quadruplex topology of any given sequence. In the present invention, isoDNA as an alternative backbone for the possible quadruplex formation and as a plausible forerunner of finding most suitable carriers of genetic information is considered for the following reasons. (1) The 2'-5' linkages maintain an extended backbone geometry due to the anomeric effect and the O4'-C1'-C2'-O2' gauche effect on the substituted sugar leading to the N-type geometry sugar conformations. (2) The guanine base orientation could be either syn or anti. (3) The 2'-5'-linkages are known to form stable loop structures in the hairpin DNA/RNA motifs, and (4) the isoDNA oligomers are relatively stable to exonuclease degradation. In a preferred embodiment, the present invention provides an aptamer/oligomer comprising a stable, non-genetic, guanine rich 2'-5' linked isoDNA. These stable, non-genetic, guanine rich 2'-5' linked isoDNA oligomers form unimolecular antiparallel G quadruplexes as studied by CD spectroscopy that maintain biological molecular recognition and is useful in therapeutics and diagnostics (Nagatoishi, S., Tanaka, Y., Tsumoto K. Circular dichroism spectra demonstrate formation of the thrombin-binding DNA aptamer G-quadruplex under stabilizing-cation-deficient conditions. Biochem. Biophys. Res. Commun. 352, 812-817, 2007). In an optional embodiment, the 2'-5' linked iso oligonucleotide is selected from isoDNA. Accordingly, the 3' deoxy 2'-5' isoDNA oligomers is selected from the group consisting of 5'-GGTTGGTTGGTTGG-2' (Seq ID No. 4); 5'-GGTGGTGTGGTGG-2' (Seq ID No. 5); and 5'-GGTG-GTGGTGG-2' (Seq ID No 6). In another embodiment, the present invention discloses hybrids involving 2'-5'-phosphodiester linkages as part of the G-quadruplex-forming sequence/oligomer. They could be in combination with 3'-5'-phosphodiester linkages in DNA/RNA, or other linkages such as in TNA, LNA, UNA, 3'-5'-linked modified backbones such as 2'-OMe, etc. The 3' deoxy 2'-5' isoDNA-isoRNA hybrid is selected from the group consisting of sequences 5% GGTTGG$^X$U$^F$GTGGTTGG-2' Id No 7; 5'-GGTTGG$^X$U$^F$G$^X$U$^F$GGTTGG-2' Id No 8; 5'-GGTTG-G'U$^F$GTGGTTGG-2' Id No 9; 5'-GGTTGG'U$^F$G'U$^F$GGT-TGG-2' Id No 10. Where $^X$U$^F$ U is 3'deoxy, 3'-xylofluoro-uridine, 'U$^F$ is 3'deoxy, 3'-ribofluoro-uridine. In another preferred embodiment, the present invention provides that the guanine-rich 2'-5'-isoDNA sequence forming 3D antiparallel quadruplex of the instant invention is a thrombin-binding oligomer or a thrombin binding aptamer (TBA). The terms oligomer and aptamer with reference to the thrombin-binding are used interchangeably, hence the person skilled in the art will appreciate the same as such. The thrombin binding oligomer or aptamer (TBA) binds and inhibits thrombin, leading to inhibition of clotting. SELEX (Systematic Evolution of Ligands by Exponential Enrichment) generated G-quadruplex-forming thrombin binding aptamer (TBA), 5'-GGTTGGTGTGGTTGG-3' (Seq ID No:1) is used as a reference to study the structural topology of the regioisomeric 2'-5' backbone (isoTBA). Accordingly, the present invention provides guanine-rich 2'-5'-isoDNA sequence having Seq ID No. 2 comprising 5'-(3'-deoxy-GGTTGGTGTGGTTGG)-2' isod-TBA-2 synthetic oligonucleotide. (Table 1). Further, by replacing 3'-deoxythymidine in the TGT loop at T7 and T9 position in Seq ID No. 2 by uridine affords UGU loop-modified sequence isod-TBA-3 (i.e. Seq ID No.3) 5'-(3'-deoxy-GGTTGGUGUG-GTTGG)-2'. In yet another preferred embodiment, the present invention provides the process for synthesizing 2'-5' linked iso oligonucleotides comprising:

a. Synthesizing 2'-5'-linked oligonucleotides (ON Id No 2, 4-6)—using 3'-deoxy-2'-ribothymidine phosphoramidites and 2'-deoxy-3'-guanosine phosphoramidites, by β-cyanoethyl phosphoramidite chemistry; Sequences Id No 3 and Id No 7-10 were synthesized using 3'-deoxy-2'-ribothymidine phosphoramidites, 3'-deoxy-2'-guano sine phosphoramidite and uridine (U)-2'-phosphoramidite, 3'-ribofluoro-3'-deoxy-uridine ($^rU^F$)-2'-phosphoramidite, 3'-xylo fluoro-3'-deoxy-uridine ($^xU^F$)-2'-phosphoramidite at appropriate positions in the sequences by β-cyanoethyl phosphoramidite chemistry.

a. Desalting the oligonucleotides after post-synthetic treatment by passing through Pharmacia NAP-5 columns followed by purification by RP-HPLC using an increasing gradient of acetonitrile in 0.1M triethylammonium acetate (pH 7.0).

b. Replacing the 3'-5'-phosphodiester linkages in control Seq ID no. 1 (dTBA-1) by 2'-5'-phosphodiester linkages to give 3'-deoxy-2'-5' oligomer 5'-GGTTGGT-GTGGTTGG-2'Seq ID No 2 (isod-TBA-2);

c. Replacing 3'-deoxythymidine in the TGT loop (T7 and T9 in isod-TBA-2) by uridine affords UGU loop-modified sequence isod-TBA-3 (Seq ID no: 3); and d. Dissolving HPLC purified and lyophilised TBA-1, iso-TBA-2 and isod-TBA-3 in phosphate buffer pH7.5 containing KCl followed by lyophilization and further dilution.

e. The process also used CD spectroscopy techniques to show the emergence of a positive band at near 295 nm characteristic of G-quadruplex by 2'-5'isoTBA sequences (sequence Id No 2 and 3) in the presence of cations similar to 3'-5'TBA (sequence Id No 1). The process also used CD spectroscopy techniques to show the emergence of a positive band at near 295 nm characteristic of G-quadruplex by 2'-5'isoTBA sequences (sequence Id No 2 and 3) in presence of thrombin similar to 3'-5'TBA (sequence Id No 1).

Accordingly, the phosphoramidites are selected from the group consisting of Uridine 3'-O-TBDMS 2'-phosphoramidite (used for modified isod-TBA-3 sequence) and 3'-deoxy-2'-phosphoramidites.

Figure 3A:
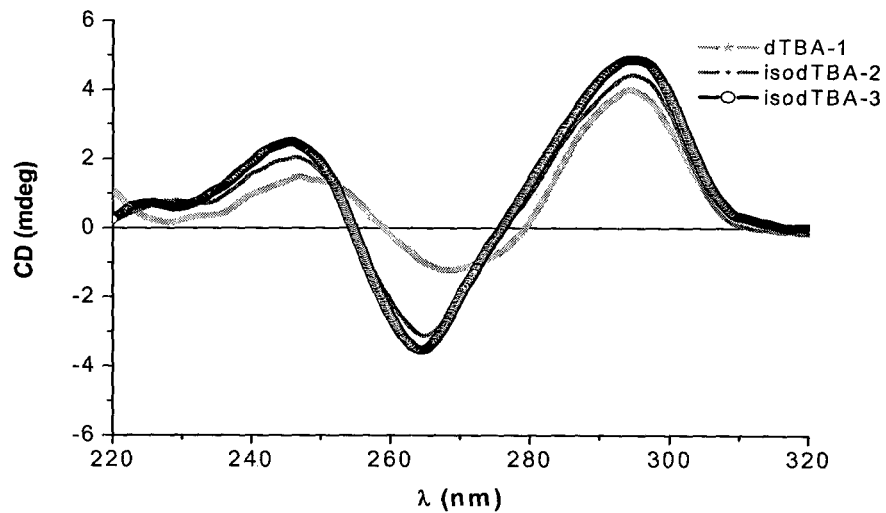
FIG. 3 A depicts the Circular Dichroism (CD) spectra of oligomers dTBA-1, isod-TBA-2 and isod-TBA-3 in K+ buffer
FIG. 3B depicts Temperature dependent changes in CD amplitude at 295 nm plotted against temperature.
Figure 3B:
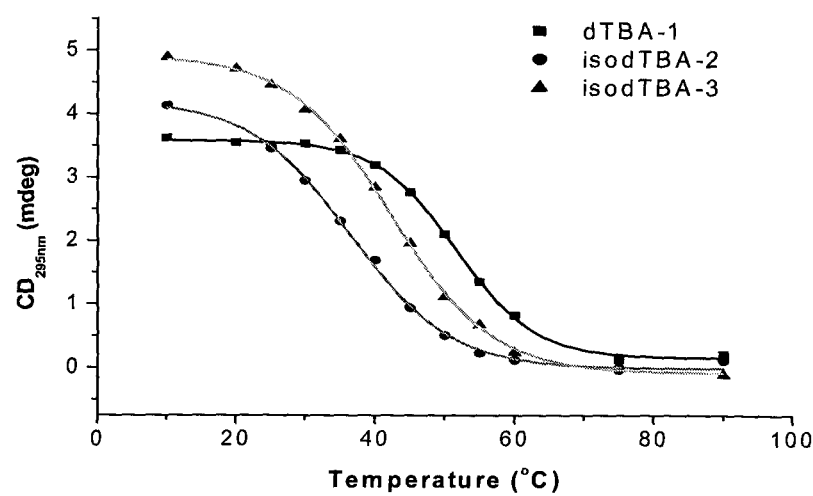
Figure 8:
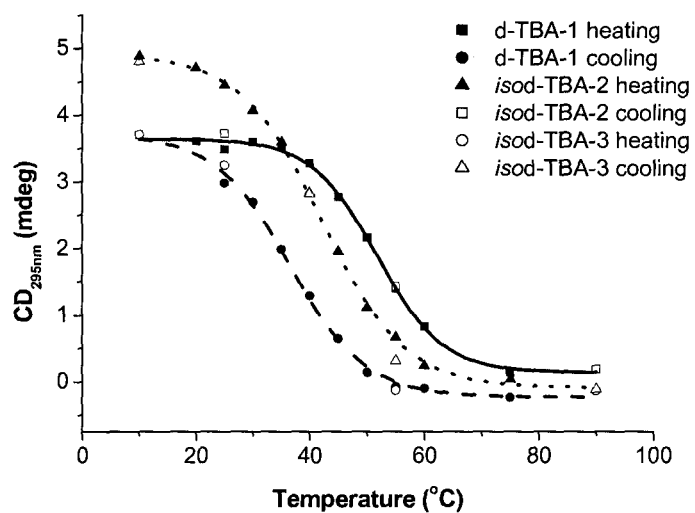
FIG. 8 depicts the CD hysteresis changes is CD amplitude at 295 nm with temperature during heating and cooling experiments for d-TBA1, isod-TBA-2, isod-TBA-3
Figure 9:
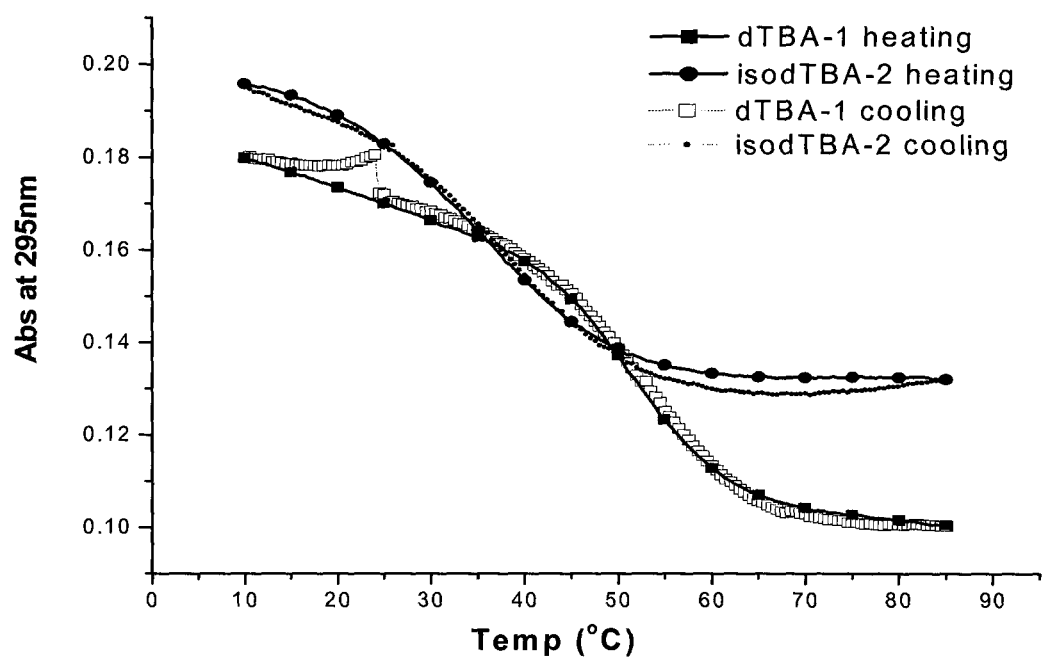
FIG. 9 depicts UV hysteresis-changes is absorbance at 295 nm during heating and cooling experiments for d-TBA1, isod-TBA-2

Further, 3'-5'-phosphodiester linkages in control sequence dTBA-1 (Seq ID No. 1) is replaced by 2'-5'-phosphodiester linkages to give 3'-deoxy-2'-5' oligomer 5'-GGTTGGT-GTGGTTGG-2' isod-TBA-2 (Seq ID No. 2). Replacement of 3'-deoxythymidine in the TGT loop (T7 and T9 in isod-TBA-2) by uridine affords UGU loop-modified sequence isod-TBA-3 (Seq ID No.3). The 3'-OH group shifts the equilibrium to S-type sugar conformation and imparts rigidity and stability to the loop similar to that imparted by the N-type sugars in DNA. In another embodiment, the present invention provides synthesis of the hybrid with 3'-5'-linked DNA. In yet another embodiment, the formation of G-quadruplex and stability of the oligomers, 2'-5'-linked isod-TBA-2 and isod-TBA-3 and control sequence d-TBA-1 of the instant invention is determined in the presence of monovalent cations and thrombin. The 2'-5'-linked isod-TBA-2 and isod-TBA-3 and control sequence d-TBA-1 are observed to exhibit intense maxima at 295 nm in CD spectra in presence of K+ ions (FIG. 3A) which correspond to the previously-described group-III antiparallel G-quadruplex topology for 3'-5'-DNA. This indicates the formation of antiparallel folded G-quadruplex in the presence of monovalent cations for isoDNA backbone. The stability of the G-quadruplexes is followed by change in the amplitude of the CD signal at 295 nm with temperature (FIG. 3B). The replacement of the TGT by the UGU in the loop region (isod-TBA-3) is observed to improve the stability of the quadruplex structure as seen by a positive change in $T_m$ in presence of K+ (Table 1) showing the influence of loop geometry on quadruplex stability as found earlier for DNA-TBA. Further, the hysteresis between the heating and cooling curves is found to be negligible in all the cases indicating unimolecular folding into G-quadruplex form (FIG. 8). The results are further supplemented by UV-$T_m$ and hysteresis measurements (FIG. 9) and also by $T_m$ experiments at differing concentrations, viz., 5 μM and 20 μM. In a further embodiment, the stability of 2'-5'-linked isod-TBA-2 and isod-TBA-3 is determined in the presence of thrombin without adding monovalent cation. The CD maximum at 295 nm which emerges for isod-TBA-2 and isod-TBA-3 and the isoelliptic points observed at 280 nm and 255 nm clearly indicate the two-state nature of the structural transition. Further, the temperature-dependent stability of the quadruplex structure determined by recording the CD amplitude at 295 nm with increasing temperature indicate the specific role of thrombin in inducing quadruplex structures and clearly point out the similarity in structural topology of isoTBA with TBA, necessary for interaction with thrombin. The characterisation and melting temperatures of G-quadruplexes of the instant invention are summarized in Table 1. In another embodiment, the stable, non-genetic, guanine rich 2'-5' linked isoDNA/RNA capable of forming G-quadruplexes are further characterised by mass spectroscopy, NMR UV-Thermal denaturation, fluorescence spectroscopy and polyacrylamide gel electrophoresis.

In another embodiment, the present invention provides use of guanine rich 2'-5' linked isoDNA/RNA for medical applications like anti-thrombin, anti-HIV, anti-proliferative, anti-cancer, Telomerase inhibition and the like. The instant of guanine rich 2'-5' linked isoDNA such as TBA is used in deep vein thrombosis, where prolonged anticoagulant activity is required. In an optional embodiment the guanine rich 2'-5' linked isoDNA/RNA of the instant invention may include pharmaceutical composition prepared by the method known in the art. In another embodiment, the present invention provides a method for the treatment of cardiovascular surgery in which anticoagulation is desired, in the treatment of HIV, cancer, as inhibitors of thrombin, telomerase comprising administering the said composition to a subject in need thereof orally, parenterally, intraperitoneally or the like. Thus, the present invention provides that the homogeneous 2'-5' linked isoDNA/RNA is capable of forming hitherto unknown unimolecular, antiparallel G-quadruplex structures that can retain the functional ability. The guanine-rich 2'-5'-isoDNA sequence can form 3D antiparallel quadruplex, having similar structural topology as the DNA quadruplexes. The G-rich isoTBA sequence not only forms stable G-quadruplex which is structurally similar to TBA but also exhibits unprecedented acceptance for a 100% isoDNA backbone while binding to a large protein, thrombin, originally evolved to function with a DNA backbone.

EXAMPLES

The following examples are given by way of illustration and should not be construed to limit the scope of the invention:

Example 1: Process for Preparation of Guanine-Rich 2'-5'-isoDNA

3'-5'- and 2'-5'-linked oligonucleotides were synthesized in-house on a Bioautomation Mermade-4 DNA synthesizer employing β-cyanoethyl phosphoramidite chemistry. The 2'-deoxy-3'-phosphoramidites, Uridine 3'-OTBDMS 2'-phosphoramidite (used for modified isod-TBA-3 sequence) were obtained from ChemGenes and 3'deoxy-2'-phosphoramidites were obtained from Glen Research. Universal columns procured from Bioautomation were used for 2'-5' oligomer synthesis. Oligonucleotides after post-synthetic treatment were desalted by passing through Pharmacia NAP-5 columns, then purified by RP-HPLC on a C18 column using a Waters system (Waters Delta 600e quaternary solvent delivery system and 2998 photodiode array detector and Empower2 chromatography software). An increasing gradient of acetonitrile in 0.1M triethylammonium acetate (pH 7.0) was used. For NMR studies, HPLC purified and lyophilised TBA-1 and iso-TBA-2 were dissolved in 150 μl of 10 mM K-phosphate buffer pH 7.5 containing 100 mM KCl and lyophilized, then diluted in 9:1 v/v $H_2O:D_2O$ (150 μl) to get a concentration of 100 μM of each oligomer.

Characterization:

1. Mass Spectrometry

Mass of the oligomers was obtained by MALDI-ToF mass spectrometry. The MALDI-ToF spectra were recorded on Voyager-De-STR (Applied Biosystems). The matrix used for analysis was THAP (2',4',6'-trihydroxyacetophenone). The result is given in Table 1 below.

2. CD Thermal Denaturation Studies of the TBA Sequences with and without Thrombin and BSA.

CD spectra were recorded on Jasco J-815 CD Spectrometer equipped with a Jasco PTC-424S/15 peltier system. 2 mm path-length quartz cuvettes were used for a sample volume 500 μl and strand concentration of 5 μM in 10 mM Na/K-phosphate buffer (pH 7.5) containing 100 mM NaCl/KCl respectively. Oligomers prepared in buffer were annealed by heating at 95° C. for 5 minutes, then slowly cooled to room temperature, followed by refrigeration for 5-6 hours before use. Spectral scans were collected over a wavelength range 200-320 nm at a scanning rate of 100 nm $min^{-1}$. The spectra were collected as an average of three scans for each sample.

Figure 5A:
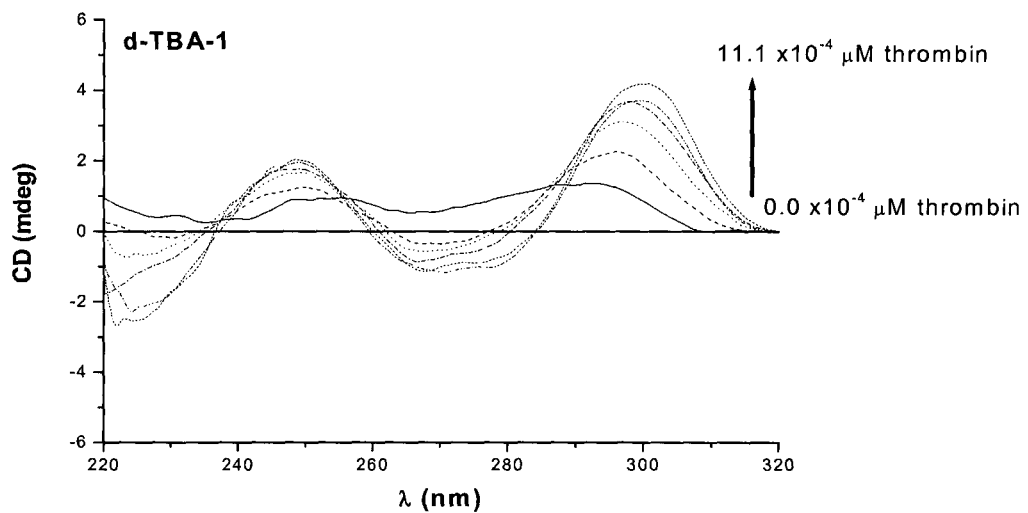
FIG. 5 depicts the changes in CD signal at 295 nm upon addition of thrombin FIG. 5a) d-TBA-1 5b) isod-TBA-2 and 5c) isod-TBA-3.
Figure 5B:
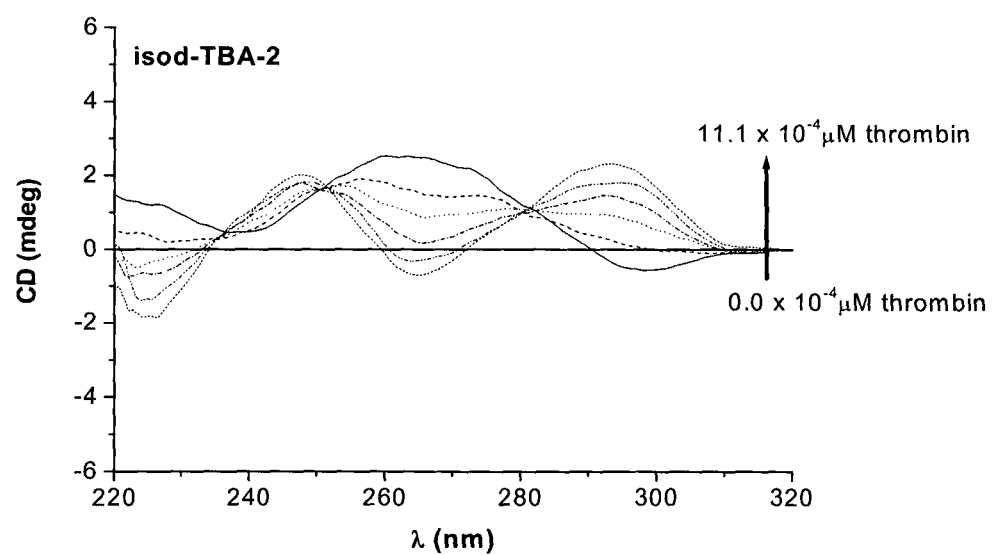
Figure 5C:
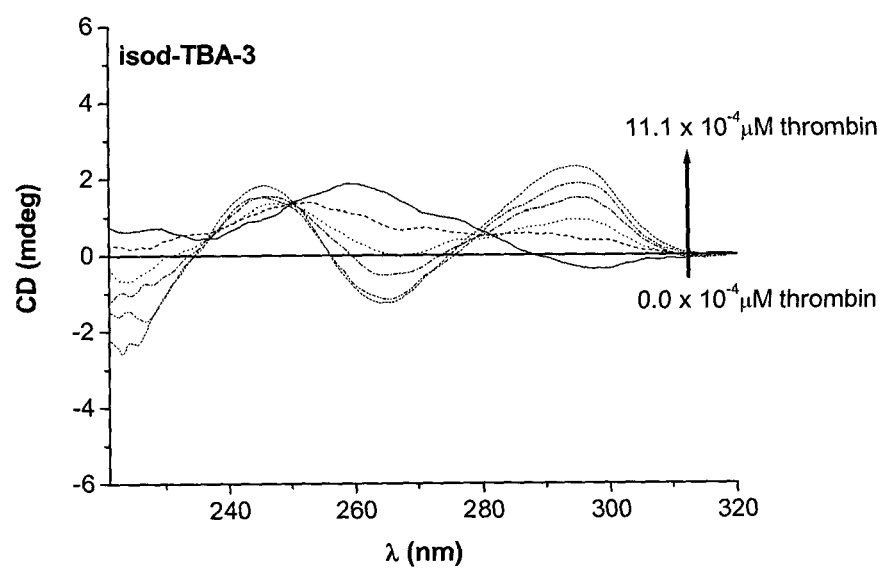

CD experiments with d-TBA-1, isod-TBA-2 and isod-TBA-3 were carried out in the presence of increasing concentrations of thrombin at low temperature (FIG. 5 a,b,c) Nagatoishi, S., Tanaka, Y., Tsumoto K. Circular dichroism spectra demonstrate formation of the thrombin-binding DNA aptamer G-quadruplex under stabilizing-cation-deficient conditions. Biochem. Biophys. Res. Commun. 352, 812-817 (2007). In the case of control d-TBA-1, a CD maximum at 295 nm was observed even in the absence of either thrombin or $K^+$, revealing the preference of G-quadruplex structure as reported earlier[10] and also as seen by $^1H$ NMR in the present studies. An increase in the CD signal amplitude upon incremental addition of thrombin is observed even at relatively low concentrations of thrombin. In case of isod-TBA-2 and isod-TBA-3, CD band at 295 nm and G-quadruplex structure was not evident in the absence of either thrombin or $K^+$, which is also supported by $^1H$ NMR. Upon incremental addition of thrombin, the CD maximum at 295 nm emerges for isod-TBA-2 and isod-TBA-3. Isoelliptic points were observed at 280 nm and 255 nm in all the cases. Further, the temperature-dependent stability of the quadruplex structure was followed by recording the CD amplitude at 295 nm with increasing temperature. The strength of d-TBA-1 G-quadruplex was the highest with $T_m=22°$ C., followed by iso-d-TBA-3 ($T_m$ 13° C.) and iso-d-TBA-2 ($T_m<10°$ C.). The CD signal at 295 nm was restored upon addition of $K^+$ and the quadruplexes were as stable as with $K^+$ alone at the thrombin concentrations used in the present study (Table 1).

TABLE 1

Oligomers synthesized with MALDI-ToF mass spectrometric characterization and melting temperatures of G-quadruplexes

| No | TBA sequences | MALDI-ToF Mass Calculated | MALDI-ToF Mass Observed | $T_m$° C. $Na^+$ | $T_m$° C. $K^+$ | $T_m$° C. Thrombin[a] |
|---|---|---|---|---|---|---|
| 1 | 5'-(2'-deoxy-GGTTGGTGTGG TTGG)-3' d-TBA-1 (Seq ID No 1) | 4726 | 4728 | 22.2 | 52.0 | 22 (53) |
| 2 | 5'-(3'-deoxy-GGTTGGTGTGG TTGG)-2' isod-TBA-2 (Seq ID No 2) | 4726 | 4731 | 24.9 | 37.1 | <10 (38) |
| 3 | 5'-(3'-deoxy-GGTTGGUGUG GTTGG)-2' isod-TBA-3 (Seq ID No 3) | 4730 | 4732 | nd | 45.0 | 13.2 (45) |

[a]Values in parenthesis are in presence of $K^+$

Figure 10A:
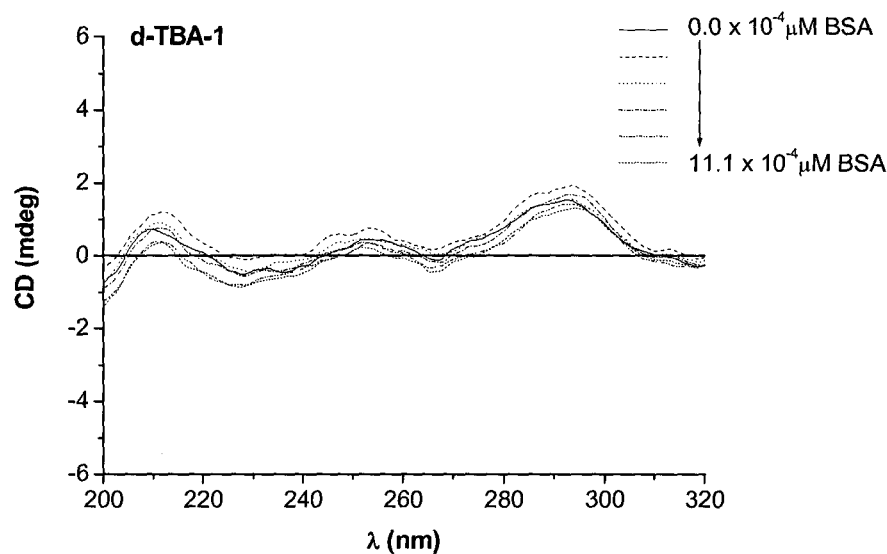
FIG. 10. A. depicts CD of d-TBA-1; B. depicts isod-TBA-2 with incremental additions of Bovine serum albumin (BSA) at 4° C.
Figure 10B:
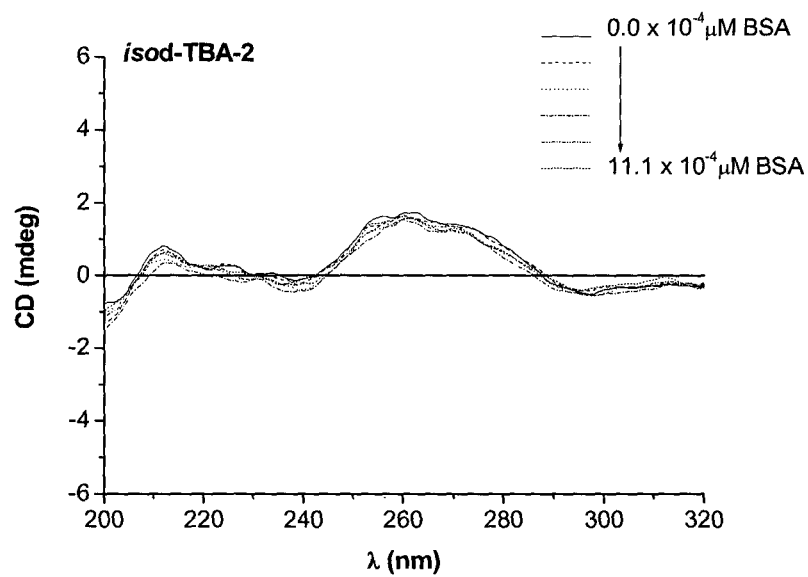

Changes in CD spectral amplitudes were not observed when serum albumin was used instead of thrombin in these experiments confirming the specific role of thrombin in inducing quadruplex structures. (FIG. 10B).

TABLE 2

List of sequences

| Id No 1 | 5'-GGTTGGTGTGGTTGG-3' |
|---|---|
| Id No 2 | 5'-GGTTGGTGTGGTTGG-2' |
| Id No 3 | 5'-GGTTGGUGUGGTTGG-2' |
| Id No 4 | 5'-GGTTGGTTGGTTGG-2' |
| Id No 5 | 5'-GGTGGTGTGGTGG-2' |
| Id No 6 | 5'-GGTGGTGGTGG-2' |
| Id No 7 | 5'-GGTTGG$^XU^F$GTGGTTGG-2' |
| Id No 8 | 5'-GGTTGG$^XU^F$G$^XU^F$GGTTGG-2' |

TABLE 2-continued

List of sequences

| Id No 9 | 5'-GGTTGG'U$^F$GTGGTTGG-2' |
|---|---|
| Id No 10 | 5'-GGTTGG'U$^F$G'U$^F$GGTTGG-2' |

3. Imino Proton NMR Spectra:

The NMR measurements were performed on a Bruker AV 500 NMR spectrometer operating at 500.13 MHz for $^1$H using a 5 mm BBFO probe. Samples (150 uL of ~100 uM solution) were prepared in a standard 3 mm NMR tube in 10% $D_2O$ and 90% $H_2O$. Water suppression was achieved by using a standard Bruker watergate W5 pulse sequence with gradients. 2000 transients were collected with an acquisition time of 3.54 sec and a pulse delay of 1 sec. The raw data were processed with a Gaussian function for improvement of signal to noise ratio. Temperature during the measurements was controlled by means of a Bruker BVT 3000 unit.

Figure 4:
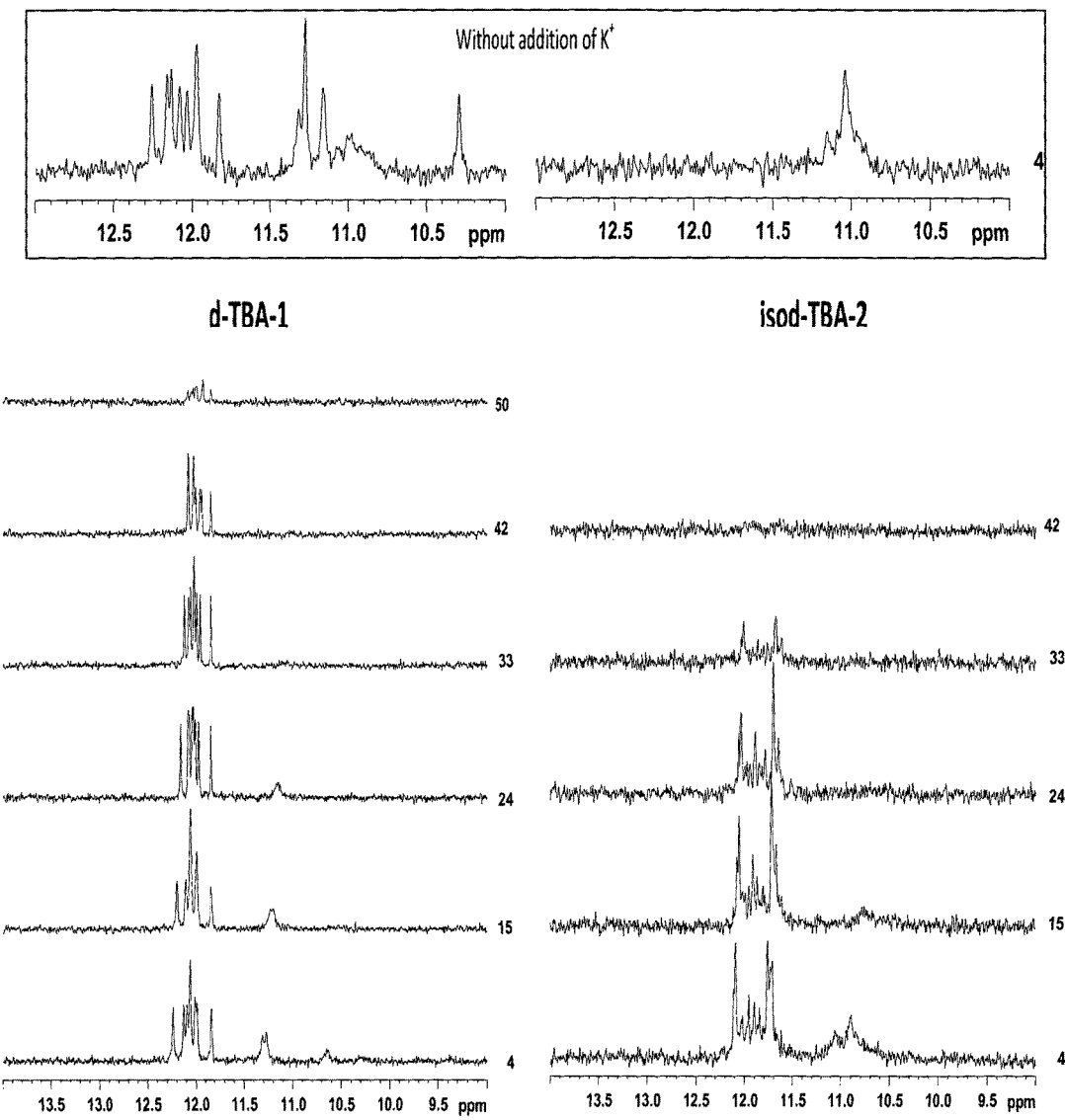
FIG. 4 depicts the quadruplex imino proton spectral region for d-TBA-1 and isod-TBA-2 in the presence of $K^+$ from 4° C. to 50° C. Inset shows the imino proton spectral region in the absence of $K^+$ at 4° C.

The characteristic chemical shifts of imino proton signals of the eight H-bonds formed between the guanines of each G-quartet of a quadruplex structure were observed between 11.5 and 12.5 ppm range in the $^1$H NMR spectrum. The imino proton chemical shifts for isod-TBA-2 were comparable with the control d-TBA-1 indicating the hydrogen-bonded quadruplex formation (FIG. 4). The temperature-dependent changes in the spectra were then recorded. As seen for the CD at 295 nm, the $^1$H NMR signals between 11.5 and 12.5 ppm slowly disappeared with increasing temperature due to the loss of quadruplex structure near $T_m$. In the case of d-TBA-1 and isod-TBA-2, the NMR signals were observed up to 50° C., and 40° C., respectively (FIG. 4).

The broad peaks between 10.5-11.1 ppm in the isod-TBA-2 and d-TBA-1 spectra disappeared much below the melting temperature (~20-25° C.) in each case, suggesting that these may not be involved in the H-bonded quadruplex structure. The appearance of characteristic H-bonded imino protons supports the fact that isod-TBA-2 does form a G-quadruplex structure. although less stable (Table 1, $T_m$ 37° C.) compared to the 3'-5'-linked d-TBA-1 (Table 1, $T_m$ 52° C.) quadruplex structure. It is evident from the $^1$H NMR signals at 4° C. between 11.5 and 12.5 ppm that d-TBA-1 has significant quadruplex structure even in the absence of $K^+$ whereas isod-TBA-2 is not structured without monovalent ions such as $K^+$ (FIG. 4, Inset).

4. UV-Thermal Denaturation Studies of the TBA Oligomers:

UV-Thermal denaturation studies of the TBA oligomers were performed using a 10 mm quartz cell in a Varian Cary 300 Bio UV-Visible Spectrophotometer. The TBA oligomers (5 µM) were annealed in a 10 mM potassium phosphate buffer, pH 7.5, 100 mM KCl. The concentration was calculated on the basis of absorbance from molar extinction coefficients of the corresponding nucleobases of DNA/isoDNA. Absorbance versus temperature profiles were obtained by monitoring the absorbance at 295 nm from 10-85° C. at a ramp rate of 0.5° C. per minute. Both melting and re-annealing profiles were obtained to check reversibility of the process. A stream of dry nitrogen was gently applied through the sample compartment to prevent condensation of water on the cuvette walls at low temperatures.

Figure 6:
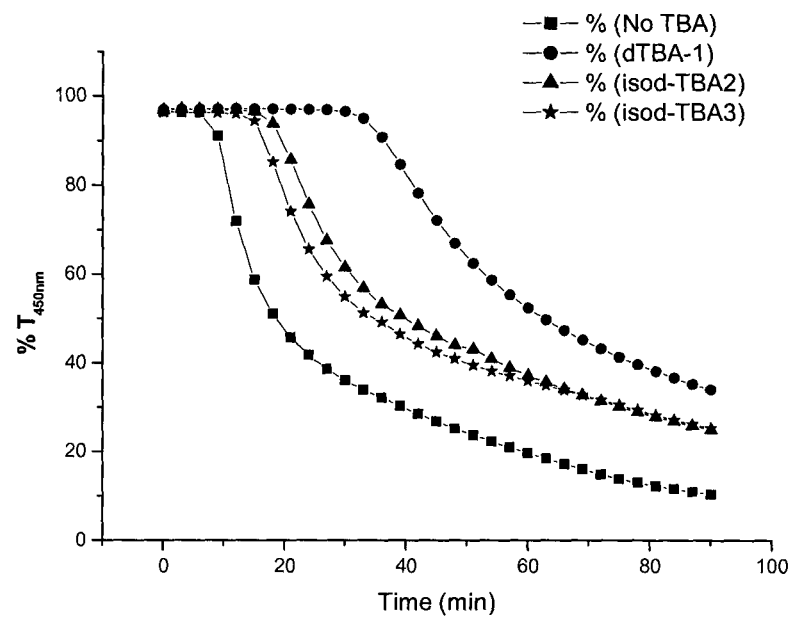
FIG. 6 depicts anti-thrombin activity measured by UV transmittance in the presence of d-TBA-1, isod-TBA-2 and isod-TBA-3.
Figure 6:
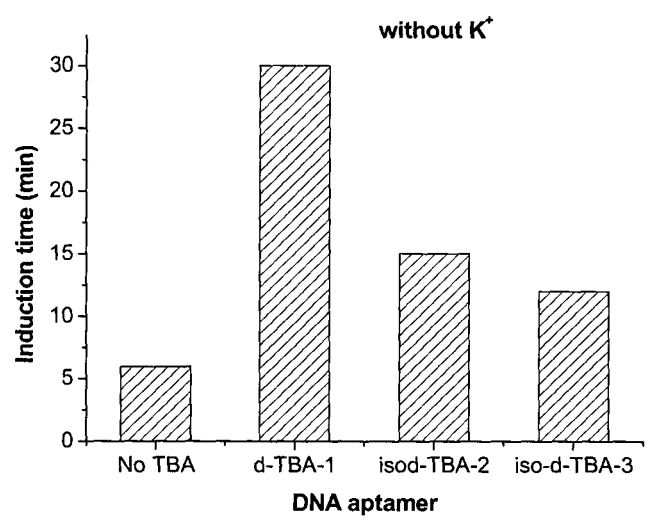
Figure 7:
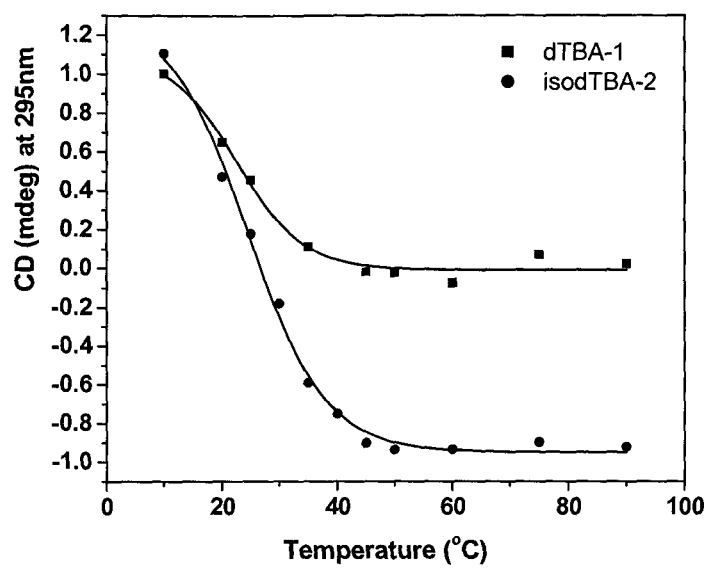
FIG. 7 depicts the CD amplitude at 295 nm versus temperature during heating to get $T_m$ of d-TBA-1 and isod-TBA-2 in presence of Na+ (5 µM strand in 10 mM Na-phosphate buffer pH 7.5 containing 100 mM NaCl).

5. Anti-Thrombin Activity Measurements:

Anti-thrombin activity measurements were done by using Varian Cary 300 Bio UV-Visible spectrophotometer to measure % transmittance change over time. 0.1 NIH unit of thrombin (50 NIH/ml, bovine thrombin, Fibroscreen reagent, Tulip Diagnostics (P) LTD.) was added to the TBA-1, iso-TBA-2 aptamers dissolved in water to a concentration of $3.7 \times 10^{-8}$M and incubated for 15 minutes at 25° C. This was then added to 1 ml fibrinogen solution (Sigma product No F 3879, $3 \times 10^{-6}$ M) in saline and the transmittance was measured at 2 minute intervals for 90 minutes. The inhibitory activity of the aptamers on thrombin-catalyzed conversion of fibrinogen to fibrin (clotting) was determined by measuring the percent transmittance with time in the absence and presence of potassium ions. d-TBA-1 slowed down the coagulation with an increased induction time ($t_i$ as coagulation parameter), confirming its reported inhibitory activity (FIG. 6). The induction time for the isoDNA oligomers isod-TBA-2 and isod-TBA-3 were considerably less than for d-TBA-1, but more than that in the absence of any aptamer, with or without $K^+$. Surprisingly, the higher thermal stability of isod-TBA-3 was not effectively reflected in its anti-thrombin activity. The experiment provides conclusive evidence that the isod-TBA oligomers are indeed capable of not only forming G-quadruplex structures but also hold similarity in structural topology capable of taking active part in the assigned function of the TBA, though less efficiently.

6. Enzymatic Stability of Aptamers to SVPD:

Enzymatic hydrolysis of the aptamers d-TBA-1, isod-TBA-2 (7.5 µM) was carried out at 37° C. in 100 µl buffer (100 mM Tris-HCl (pH 8.5), 15 mM $MgCl_2$, 100 mM NaCl) and SVPD (Snake Venom phosphordiesterase) (2 µg, 1.2× $10^{-4}$ U) Aliquots were taken at several time intervals. Each aliquot was heated at 90° C. for 2 min to inactivate the nuclease enzyme. The intact oligomer at each time interval was monitored by RP-HPLC. Percentage of intact oligomer was plotted against time to show the degradation of oligomers with respect to time.

Figure 11:
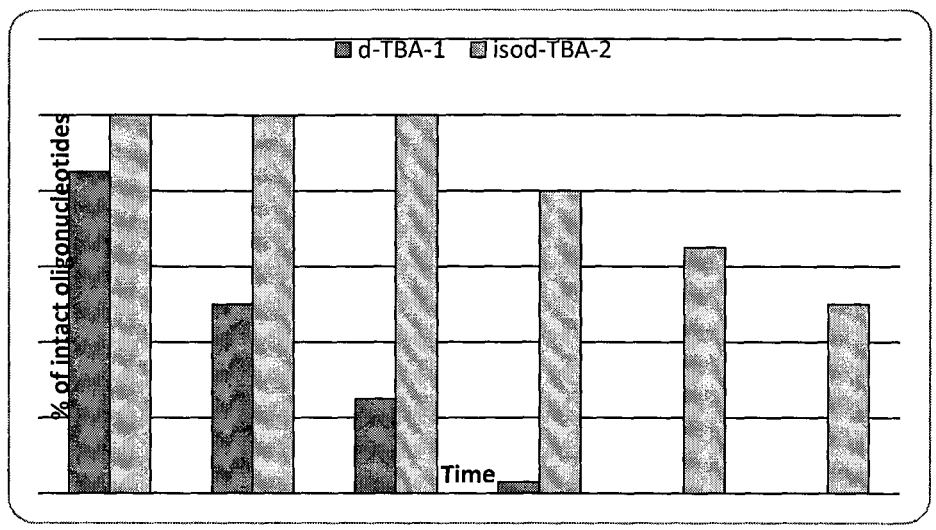
FIG. 11 depicts stability of the aptamers d-TBA-1, isod-TBA-2 towards snake venom phosphodiesterase (SVPD) enzyme.

To test the enzymatic stability of the isoDNA quadruplex-forming backbone as compared to the 3'-5'-DNA quadruplexes, the aptamers of the instant invention were treated to SVPD digestion (FIG. 11). The 2'-5'-linked isoDNA oligomer isod-TBA-2 was found to be digested much slower compared to the control d-TBA-1. The half-life of isoTBA-2 was found to be ~120 min (FIG. 11) while that of TBA-1 was found to be ~20 min at 37° C. The observed higher stability of the isoDNA oligomer offers obvious advantages for applications in biological systems, when the control unmodified oligomer has a relatively low half-life.

Figure 12:
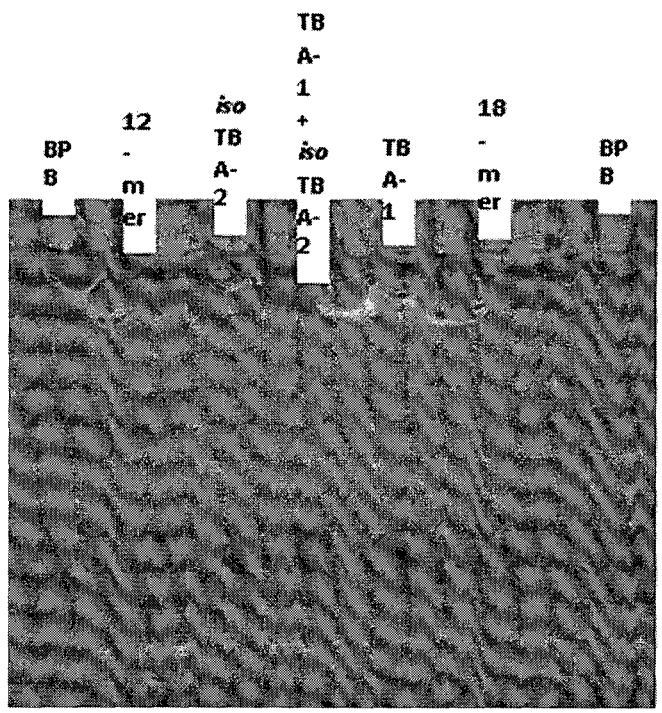
FIG. 12 depicts non-denaturing PAGE analysis showing the relative mobilities of TBA-1 and isoTBA-2. (a) visualized by UV shadowing and (b) visualized by ethidium bromide staining.
Figure 12:
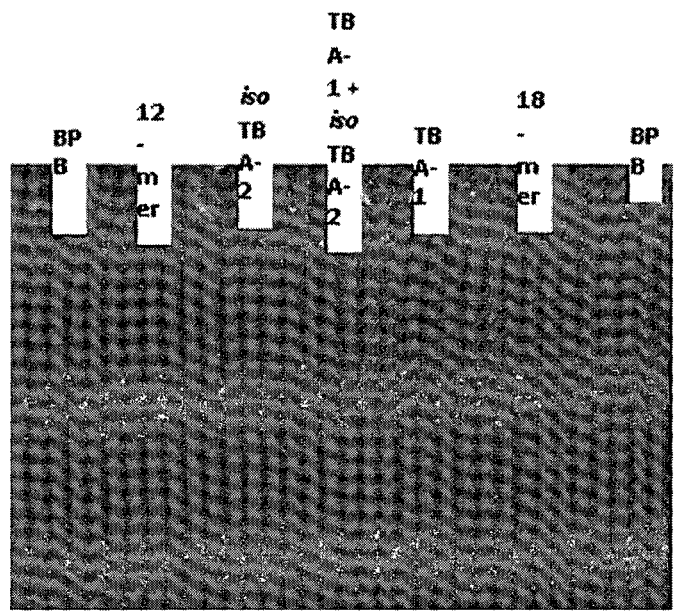
Figure 13:
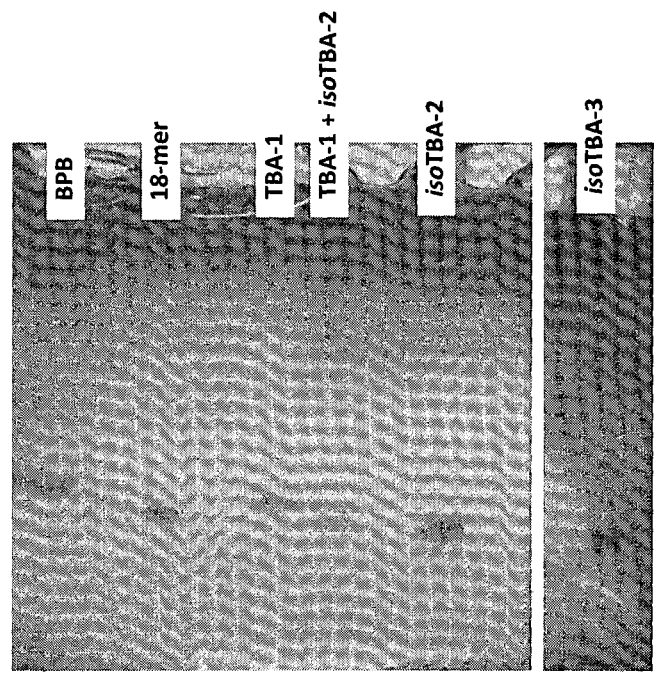
FIG. 13 depicts non-denaturing PAGE analysis showing the quadruplex formation by TBA-1, isoTBA-2 and isoTBA-3, visualized by UV-shadowing.

7. Non-Denaturing Gel Electrophoresis Study:

The quadruplex-forming ability of the synthesized oligomers was assessed by non-denaturing polyacrylamide gel electrophoresis (PAGE). As reference oligonucleotides, two oligomers of differing lengths, viz., 5'-dAAC-CGATTTCAG-3' (12-mer) and 5'-dCACCATTGTCA-CACTCCA-3' (18-mer) were used. The TBA and isoTBA oligomers were annealed in buffer prior to loading on the gel. PAGE analysis indicated similar complex formation in the case of TBA-1 and isoTBA-2, evident from their similar mobility in gel. The gels were visualized by UV-shadowing and ethidium bromide staining (FIGS. 12 A and B). Thus, quadruplex formation was also confirmed by PAGE analysis for the oligomers of the current study (FIG. 13).

ADVANTAGE OF THE INVENTION

1. Stable to enzymatic degradation, non-genetic 2'-5' linked isoDNA oligomers capable of forming unimolecular antiparallel G quadruplexes which maintain biological molecular recognition and is useful in therapeutics and diagnostics.

We claim:

1. G-quadruplex forming isoDNA oligomers comprising a stable, non-genetic, guanine rich 2'-5' linked isoDNA sequence selected from a 3' deoxy 2'-5' isoDNA sequence and a 3' deoxy 2'-5' isoDNA-isoRNA hybrid sequence, wherein the G-quadruplex forming isoDNA oligomers are configured to bind thrombin, and
   wherein the 3' deoxy 2'-5' isoDNA sequence is selected from the group consisting of 5'-GGTTGGUGUGGTTGG-2',  Seq ID No: 3

5'-GGITGGTTGGTTGG-2',  Seq ID No: 4

5'-GGTGGTGTGGTGG-2',  Seq ID No: 5
   and

5'-GGTGGTGGTGG-2',  Seq ID No: 6 or
   the 3' deoxy 2'-5' isoDNA-isoRNA hybrid sequence is selected from the group consisting of 5'-GGTTGG$^X$U$^F$GTGGTTGG-2',  Seq ID No: 7

5'-GGTTGG$^X$U$^F$G$^X$U$^F$GGTTGG-2',  Seq ID No: 8

5'-GGTTGG'U$^F$GTGGTTGG-2',  Seq ID No: 9
   and

5'-GGTTGG'U$^F$G'U$^F$GGTTGG-2'.  Seq ID No: 10

2. The G-quadruplex forming isoDNA oligomers of claim 1, wherein the 2'-5' linked isoDNA sequence forms unimolecular antiparallel G quadruplexes.

3. The G-quadruplex forming isoDNA oligomers of claim 1, wherein the 2'-5' linked isoDNA sequence forms hybrids with isoRNA.

4. The G-quadruplex forming isoDNA oligomers of claim 1, wherein the 2'-5' linked isoDNA sequence is Seq ID NO: 2 or Seq ID NO: 3.

5. A medicament for the treatment of deep vein thrombosis comprising the G-quadruplex forming isoDNA oligomers of claim 1.

6. A composition comprising the G-quadruplex forming isoDNA oligomers of claim 1 and one or more pharmaceutically acceptable excipients.

* * * * *